United States Patent [19]
Green et al.

[11] Patent Number: 5,569,283
[45] Date of Patent: Oct. 29, 1996

[54] SURGICAL CUTTING INSTRUMENT WITH GUARDED BLADE

[75] Inventors: David T. Green, Westport; Salvatore Castro, Seymour; Keith Ratcliff, Sandy Hook; Graham W. Bryan, Norwalk; Paul Nolan, Wilton, all of Conn.

[73] Assignee: United States Surgical Corporation, Norwalk, Conn.

[21] Appl. No.: 412,599

[22] Filed: Mar. 29, 1995

Related U.S. Application Data

[63] Continuation of Ser. No. 116,779, Sep. 3, 1993, abandoned.

[51] Int. Cl.[6] ............ A61B 17/32; B26B 3/06; B26B 29/00
[52] U.S. Cl. ............ 606/170; 606/167; 30/162; 30/286
[58] Field of Search .................. 606/167, 184, 606/170, 185, 171, 705, 174; 128/4, 6; 30/162, 335, 286, 278

[56] References Cited

U.S. PATENT DOCUMENTS

| | | | |
|---|---|---|---|
| 379,286 | 3/1888 | Runnels . | |
| 495,668 | 4/1893 | Fete . | |
| 518,600 | 4/1894 | Hallman . | |
| 769,829 | 9/1904 | Mott | 606/171 |
| 2,675,595 | 4/1954 | Dyckjaer . | |
| 3,900,022 | 8/1975 | Widran . | |
| 3,902,498 | 9/1975 | Niederer | 606/170 |
| 3,995,619 | 12/1976 | Glatzer | 606/171 |
| 4,137,920 | 2/1979 | Bonnet . | |
| 4,201,213 | 5/1980 | Townsend . | |
| 4,258,716 | 3/1981 | Sutherland . | |
| 4,275,735 | 6/1981 | Chutter . | |
| 4,289,132 | 9/1981 | Rieman . | |
| 4,290,427 | 9/1981 | Chin . | |
| 4,368,734 | 1/1983 | Banko | 606/170 |
| 4,423,727 | 1/1984 | Widran et al. . | |
| 4,461,280 | 7/1984 | Baumgartner . | |
| 4,473,076 | 9/1984 | Williams et al. . | |
| 4,474,174 | 10/1984 | Petruzzi . | |
| 4,497,320 | 2/1985 | Nicholson et al. . | |
| 4,499,898 | 2/1985 | Knepshield et al. . | |
| 4,499,899 | 2/1985 | Lyons, III . | |
| 4,501,274 | 2/1985 | Skjaerpe . | |
| 4,516,575 | 5/1985 | Gerhard et al. | 606/172 |
| 4,580,563 | 4/1986 | Gross . | |
| 4,603,694 | 8/1986 | Wheeler . | |
| 4,620,547 | 11/1986 | Boebel . | |
| 4,723,546 | 2/1988 | Zagorski . | |
| 4,726,370 | 2/1988 | Karasawa et al. . | |
| 4,819,620 | 4/1989 | Okutsu . | |
| 4,923,441 | 5/1990 | Shuler | 606/170 |
| 4,924,882 | 5/1990 | Donovan . | |
| 4,962,770 | 10/1990 | Agee et al. . | |
| 4,963,147 | 10/1990 | Agee et al. . | |
| 4,990,148 | 2/1991 | Worrick, III et al. | 606/170 |

(List continued on next page.)

FOREIGN PATENT DOCUMENTS

| | | |
|---|---|---|
| 2087820 | 1/1993 | Canada . |
| 0546767 | 6/1993 | European Pat. Off. . |
| 2737014 | 8/1977 | Germany . |
| 9310704 | 6/1993 | WIPO . |

OTHER PUBLICATIONS

Paine, Kenneth W. and Polyzoidis, Konstantinos S., "Carpal Tunnel Syndrome", J. Neurosurg., vol. 59, Dec. 1983, pp. 1031–1036.

Neurosurgical Instruments, Ruggles Corporation.

*Primary Examiner*—Michael Powell Buiz
*Assistant Examiner*—Glenn Dawson

[57] ABSTRACT

A surgical cutting instrument for performing endoscopic procedures such as carpal tunnel release. The cutting instrument consists of a tubular sheath or obturator constructed of a transparent material which is connected to a handle which includes means for securing a viewing instrument such as an endoscope thereto. A cutting blade is moved from a first protected or enclosed position to a second armed position, where only the blade edge is exposed at an opening in the obturator.

34 Claims, 5 Drawing Sheets

U.S. PATENT DOCUMENTS

| | | |
|---|---|---|
| 5,029,573 | 7/1991 | Chow . |
| 5,053,044 | 10/1991 | Mueller et al. . |
| 5,061,238 | 10/1991 | Shuler . |
| 5,089,000 | 2/1992 | Agee et al. . |
| 5,112,346 | 5/1992 | Hiltebrandt et al. . |
| 5,160,318 | 11/1992 | Shuler . |
| 5,171,250 | 12/1992 | Yoon . |
| 5,171,255 | 12/1992 | Rydell . |
| 5,171,316 | 12/1992 | Mehigan . |
| 5,176,695 | 1/1993 | Dulebohn . |
| 5,179,963 | 1/1993 | Berger . |
| 5,250,061 | 10/1993 | Michelson . |
| 5,250,065 | 10/1993 | Clement et al. . |
| 5,269,796 | 12/1993 | Miller et al. . |
| 5,273,024 | 12/1993 | Menon et al. . |

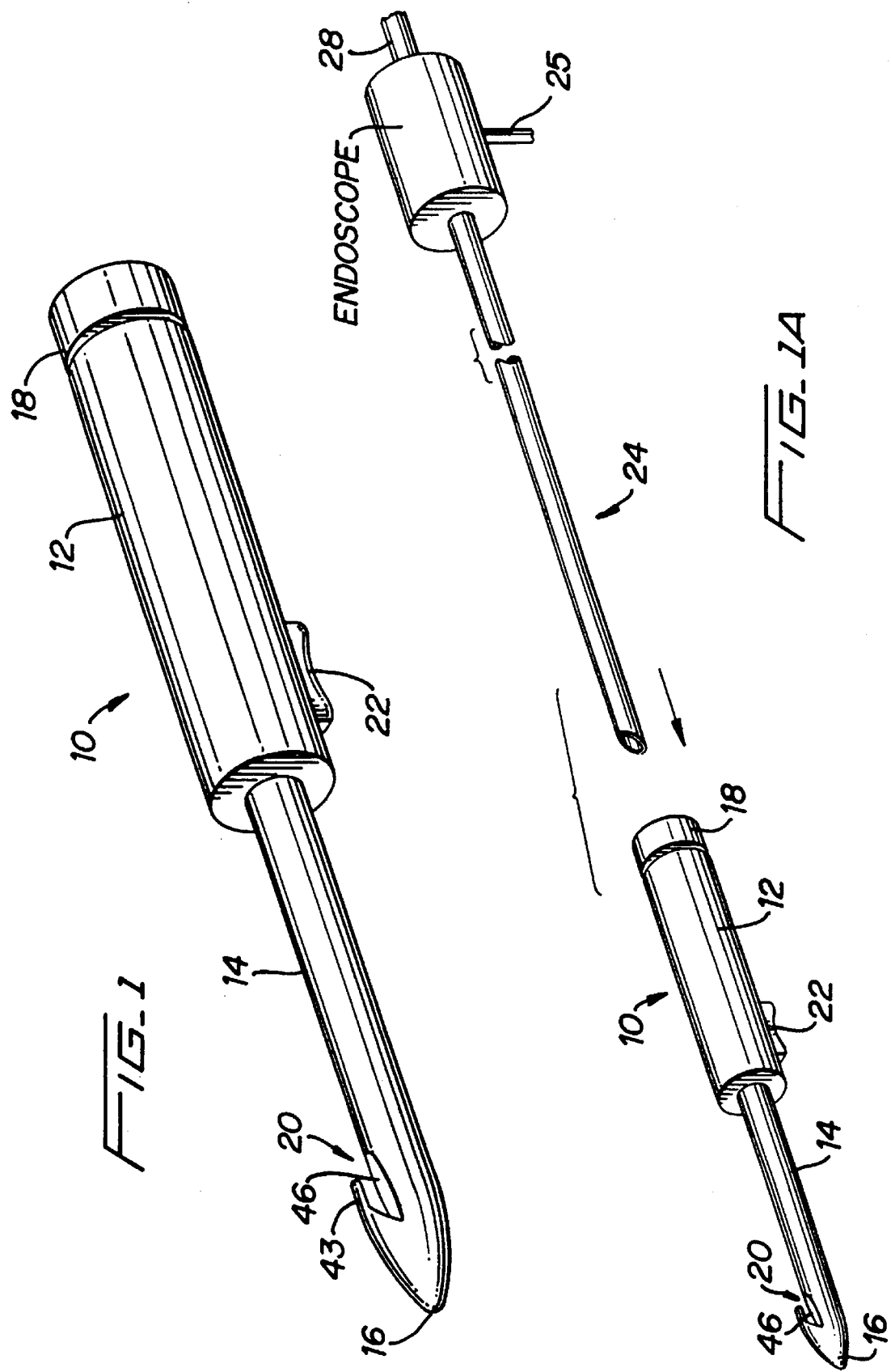

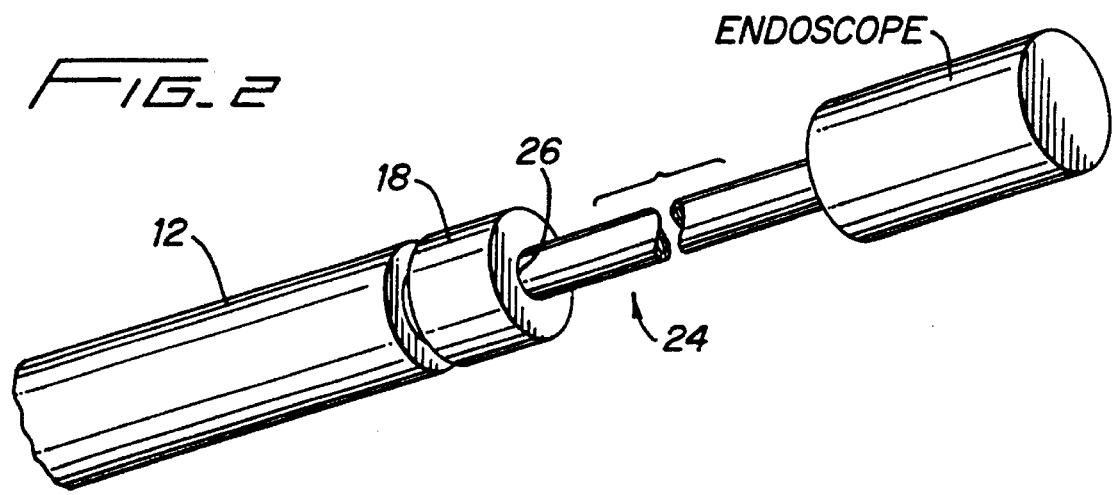
FIG_2
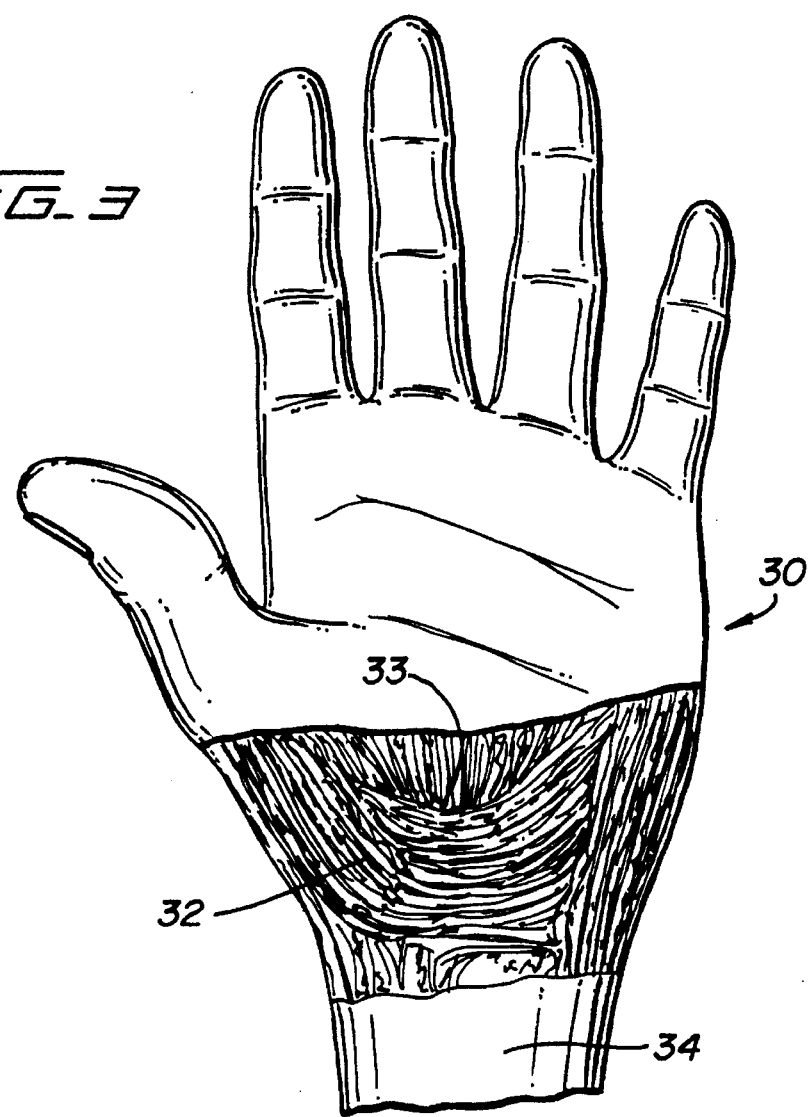
FIG_3

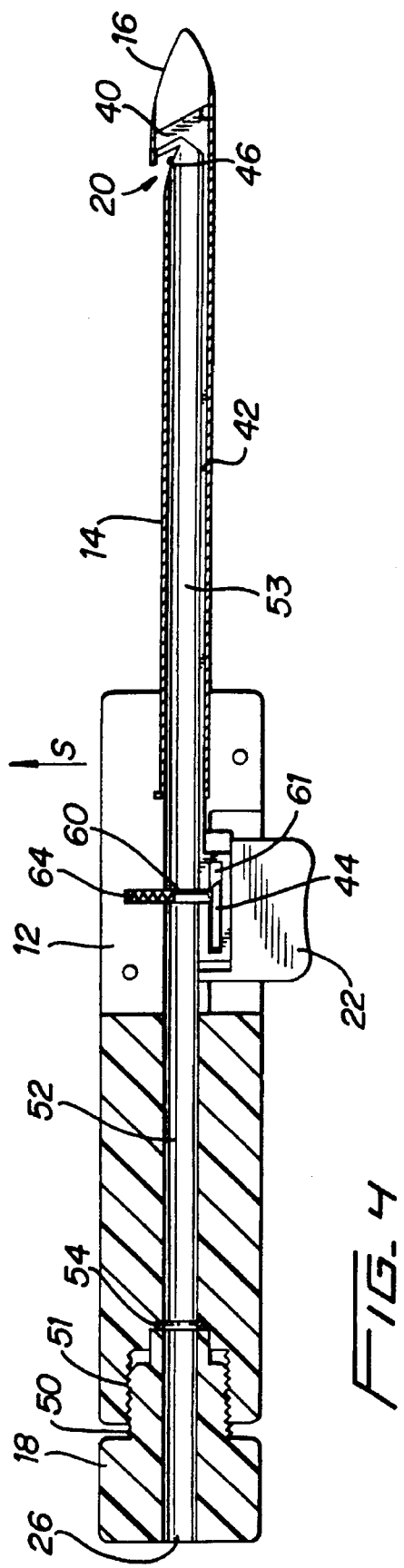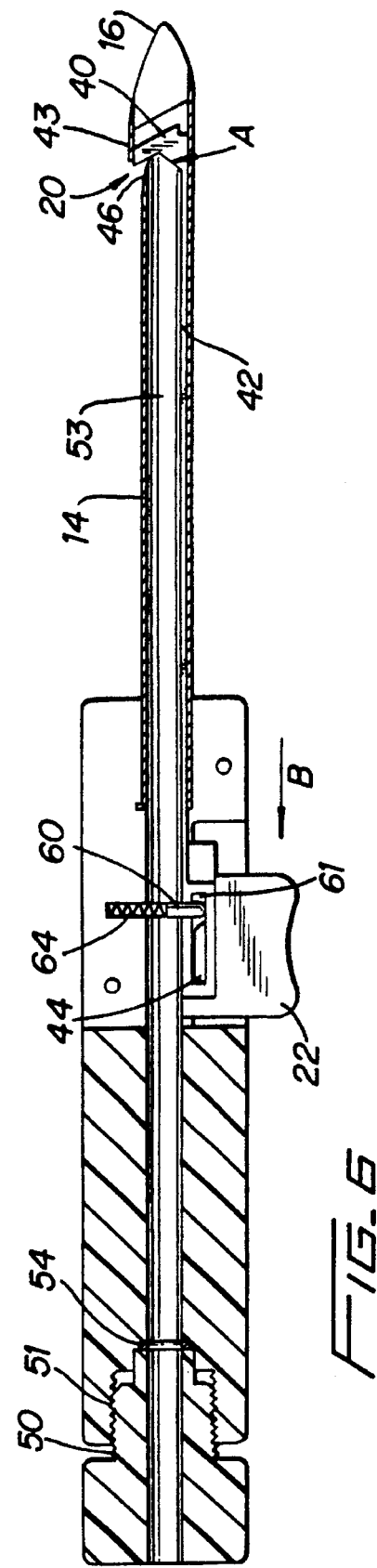

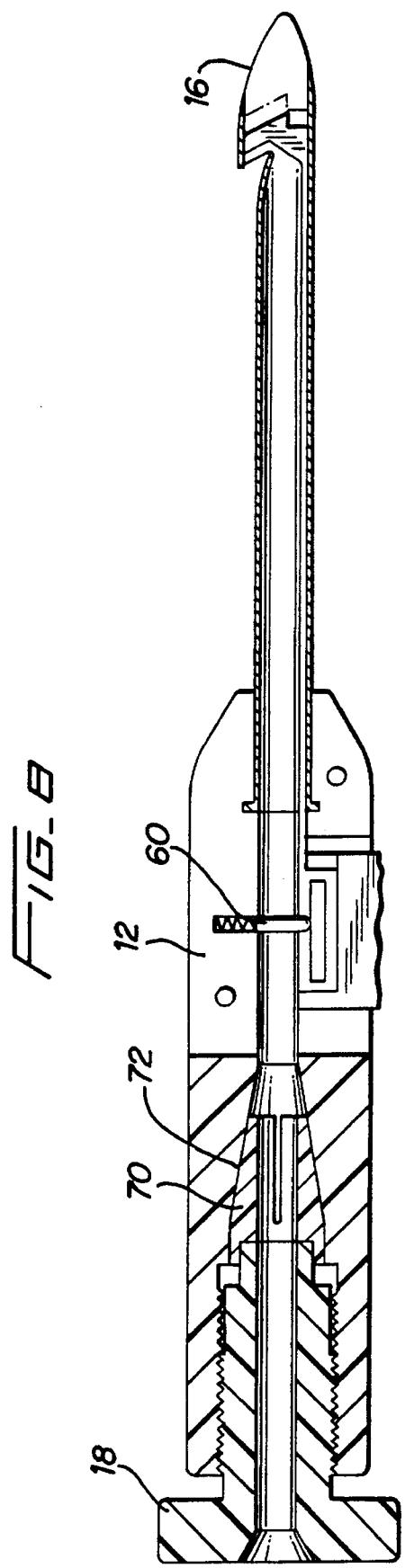

5,569,283

SURGICAL CUTTING INSTRUMENT WITH GUARDED BLADE

This is a continuation of application Ser. No. 08/116,779 filed on Sep. 3, 1993, now abandoned.

BACKGROUND OF THE INVENTION

1. Field of the Invention

The present invention relates to surgical cutting instruments for cutting tissue, and more particularly to an instrument for use with an endoscope for cutting ligaments or muscles such as the ligaments in the hand during surgical procedures such as endoscopic carpal tunnel release.

2. Discussion of the Related Art

Endoscopic surgical cutting instruments for performing surgical procedures such as carpal tunnel release are well known in the art. These devices typically include a cutting blade which is extendible or pivotable from an end portion of the instrument and is used to decompress the carpal tunnel in the hand.

Carpal tunnel syndrome is a condition of the hand which typically results in loss of feeling, weakness or numbness (paresthesia) in the fingers and hand. In general, repetitive, short stroke motion of the fingers and hand may lead to irritation of the median nerve which passes through the carpal tunnel, and this irritation or inflammation may lead to pain, weakness of the muscles and general numbness in the fingers and hand. The carpal tunnel is an area in the hand adjacent the wrist which is bounded by the carpal bones of the hand and the transverse carpal ligament. The median nerve and flexor tendons pass through the tunnel to control movement of the fingers. As the median nerve becomes irritated, or as the transverse carpal ligament is thickened due to repetitive motions of the hand and wrist, compression of the nerve inside the carpal tunnel leads to carpal tunnel syndrome and its associated degenerative conditions.

In order to treat carpal tunnel syndrome, it has been known to cut or divide the transverse carpal ligament, also known as the flexor retinaculum, to provide for decompression of the carpal tunnel. Historically, the division of the transverse carpal ligament was done during open surgical procedures which involved slitting the palm of the hand to expose the ligament prior to cutting the ligament. Recently, instrumentation has been developed to allow this procedure to be performed endoscopically, with a small incision at the base of the wrist to allow for division of the ligament beneath the skin. Once the ligament is cut, it allows for additional space in the carpal tunnel area to relieve the irritation and pressure on the median nerve.

Several instruments are known for performing endoscopic decompression by division of the transverse carpal ligament. An instrument known as the Paine retinaculotome, as described in the Journal of Neurosurgery, Vol. 59, Dec. 1983, pp. 1031–1036, provides a cutting edge which is engagable with the transverse carpal ligament on the wrist side of the ligament. The Paine instrument is inserted into the hand through an incision at the base of the wrist. As the ligament is engaged by the cutting instrument, the instrument is advanced forward into the hand to divide the ligament. A similar instrument is disclosed in U.S. Pat. No. 5,029,573 to Chow which provides a cannula that is inserted into the hand at the base of the wrist and includes a longitudinal slot in the cannula to allow for a cutting instrument to be inserted into the cannula. The instrument may be advanced through the ligament to divide the ligament, or may be inserted into the distal end of the cannula which protrudes from the palm of the patient so that the cutting instrument may be drawn through the ligament as the cutting instrument extends through the slot in the cannula.

As disclosed in U.S. Pat. Nos. 4,962,770, 4,963,147 and 5,089,000 to Agee et al., an endoscopic instrument for performing carpal tunnel release is provided which includes a pivotable cutting blade which extends outside the sheath to effect cutting of the transverse carpal ligament. An endoscope may be provided for viewing the surgical site. A disadvantage of these instruments is that the blade of the cutting instrument is exposed in such a manner that the control of the instrument to prevent cutting of tissues other than the transverse carpal ligament is minimal, and in effect will allow cutting of any tissue which happens to be in the way of the blade.

Furthermore, these known instruments either require the use of numerous components, such as that disclosed in the Chow patent, or provide instruments with numerous moving parts, such as that disclosed in the Agee et al. patents, which reduce the control of the instrument in the confined area of the carpal tunnel.

Other surgical cutting instruments are known which provide for cutting tissue by pinching the tissue between a cutting blade and a wall or stop member of the instrument. Such an instrument is disclosed in U.S. Pat. No. 5,176,695 to Dulebohn which discloses a hook like cutting member which is drawn across a gap in the end of the instrument to hook tissue such as blood vessels. The blood vessels are engaged in the gap against a wall of the instrument to cut the tissue against the wall. Similar instruments are shown in U.S. Pat. No. 3,902,498 to Niederer, U.S. Pat. No. 3,995,619 to Glatzer, and U.S. Pat. No. 4,620,547 to Boebel. A disadvantage of these instruments lies in the fact that they can only cut vessels or other tissues that will fit into the gap so that the tissue may be pinched between the cutting edge and the wall against which the cutting edge is forced.

As disclosed in U.S. Pat. No. 769,829 to Mott, a surgical instrument is provided having a head which houses a rearwardly directed cutting blade which is exposed upon movement of the head away from a housing. As the head is moved away from the housing, an opening or gap is defined between the head and the housing so that the blade may be drawn rearwardly to cut vessels or tissues that are positioned within the gap as the blade moves rearwardly against the housing. This instrument suffers the same disadvantages as the instruments described above which pinch tissue or vessels between the cutting blade and a wall of the instrument.

The need exists for a cutting instrument which obviates the disadvantages encountered in the prior art and provides a highly controllable instrument for performing endoscopic surgical procedures such as carpal tunnel release. The instrument should protect the surrounding tissue and ensure that only the tissue intended to be cut, such as the transverse carpal ligament, is cut without damaging surrounding tissue. The instrument should also provide a means for removing the instrument without injuring tissue during its removal. The instrument should advantageously enable the surgical site to be viewed during cutting if used endoscopically.

SUMMARY OF THE INVENTION

The present invention overcomes the drawbacks and deficiencies of known instruments and provides a novel cutting instrument for use in endoscopic surgical procedures such as carpal tunnel release. The instrument provides means for advancing the instrument through tissue without snagging the instrument or inadvertently cutting or damaging tissue while the instrument is being positioned. The instrument also provides means for guarding or protecting the cutting blade to permit the incision of only the target tissue, without damaging surrounding tissue which is not the object of the surgical procedure. The instrument further enables viewing the surgical procedure endoscopically, and preferably for viewing the procedure in a 360° field of vision.

The cutting instrument of the present invention provides a tubular sheath member having a cutting blade disposed therein, where the sheath is closed at its distal end. The blade has a cutting edge which is completely enclosed within the sheath in a first position, and is movable to a second position where only the blade cutting edge is exposed at the aperture. Preferably, the closed distal end tapers to a point so that the sheath acts as an obturator to permit advancing the instrument through confined areas such as the carpal tunnel. Preferably, the aperture is rearwardly directed; that is, the opening faces in the proximal direction. As the blade is moved from the first position where it is completely enclosed within the sheath to the second position, only the blade cutting edge is exposed at the aperture and faces in a proximal direction. A spring loaded detent may be provided to hold the cutting blade at either of its two positions.

In the preferred embodiment, the sheath is constructed of a transparent material such as glass or a clear plastic, and the sheath extends from a handle member. The sheath member has a longitudinal bore which communicates with a longitudinal bore which extends through the handle, to permit an endoscope to be passed through the handle and into the sheath. The transparent sheath provides a field of vision of 360° to allow the surgeon to view the surgical procedure from the time the instrument enters the patient's body to completion of the procedure. The handle may include a locking mechanism which will fix the endoscope in position in the longitudinal bore. In addition, the handle may include an actuation knob which is provided to move the blade member from the protected position to the exposed position.

In use, the instrument is utilized to perform surgical procedures such as endoscopic carpal tunnel release, to decompress the carpal tunnel and to provide relief from carpal tunnel syndrome. The instrument is inserted through an incision at the base of the wrist, and the tapered distal end allows the instrument to pass through the carpal runnel which is defined by the carpal bones of the hand on one side and is bounded on the other side by the transverse carpal ligament (also known as the flexor retinaculum). Through the provision of the endoscope, the surgeon may position the instrument so that the sheath member passes through the carpal tunnel, and is positioned so that the aperture in the sheath is adjacent the transverse carpal ligament on the finger side of the ligament. Once in position, the blade cutting edge is moved proximally into position adjacent the opening so that only the cutting edge is exposed against the transverse carpal ligament. Once in this position, the entire instrument is withdrawn to permit the blade edge while under visualization, to cut the transverse carpal ligament to decompress the carpal runnel. After the ligament is severed, the blade is returned to its initial, fully enclosed position, and the instrument is withdrawn through the original incision.

The novel cutting instrument of the present invention provides for a full view of the surgical procedure and minimizes damage to surrounding tissue by providing protection against inadvertent snagging or cutting of tissue other than the surgical objective. The cutting edge is protected at all times, and is exposed only adjacent the aperture when it is desired to cut tissue.

BRIEF DESCRIPTION OF THE DRAWINGS

The foregoing features of the present invention will become more readily apparent and may be understood by referring to the following detailed description of illustrative embodiments of the surgical cutting instrument and its novel construction, taken in conjunction with the accompanying drawings, in which:

FIG. 1 illustrates a perspective view of the instrument of the present invention;

FIG. 1A illustrates a perspective view of both a conventional endoscope and the instrument of the present invention prior to receiving the endoscope;

FIG. 2 illustrates a perspective view of the proximal end of the instrument of the present invention with a conventional endoscope (shown in block diagram) positioned therein;

FIG. 3 illustrates a perspective view of a hand in partial section showing the muscular structure and fascia structure;

FIG. 4 illustrates a cross-sectional view of the instrument of FIG. 1 showing the blade in the protected undeployed position;

FIG. 6 illustrates a cross-sectional view of the instrument of FIG. 1 with the blade in the armed or cutting position;

FIG. 8 is a cross-sectional view of an alternate embodiment of the instrument of the present invention utilizing a collet for securing the endoscope.

DETAILED DESCRIPTION OF THE PREFERRED EMBODIMENTS

Figure 5:
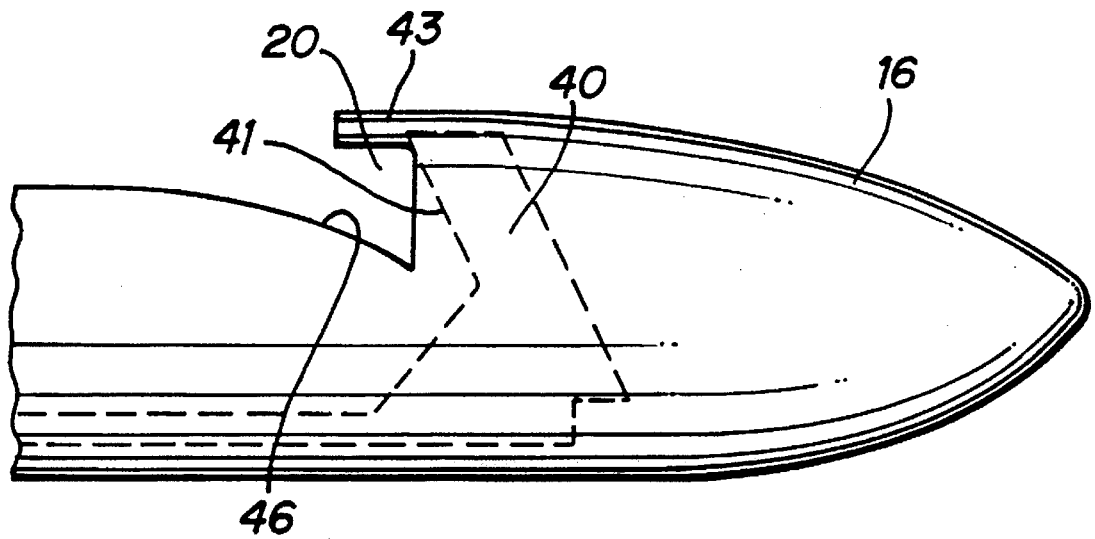
FIG. 5 is an enlarged view of the distal end of the instrument of the present invention showing the blade (in phantom) in the position of FIG. 4.

Referring now in specific detail to the drawings, in which like reference numerals identify similar or identical elements throughout the several views, FIG. 1 shows the cutting instrument 10 of the present invention. Instrument 10 includes a handle 12 from which extends a tubular sheath member 14. Sheath 14 terminates at its distal end in a tapered tip portion 16, which functions as an obturator as discussed below. Sheath 14 is attached to handle 12 by welding, screwing or any other suitable means. At the proximal end of instrument 10 is a locking nut 18 for securing an endoscope within handle 12 and sheath 14. Sheath 14 is further provided with an aperture 20 which is preferably rearwardly directed, i.e. opens towards the proximal end of the instrument, and is transverse to the longitudinal axis of the instrument to allow passage of a cutting blade as described below. An actuation knob 22 is provided to move the cutting blade into and out of position within aperture 20.

FIGS. 1A and 2 show attachment of instrument 10 to a conventional endoscope 24 (shown in block diagram), preferably 4 mm in diameter, such as the 4 mm 30° Smith & Nephew and the Storz 4mm 30° endoscopes. The endoscope 24 is preferably rigid and includes a connector 25 for connection to a light source for illuminating the surgical site and a connector 28 for connection to a video screen to enable the viewing of the surgical procedure. The endoscope 24 is preferably a 30° fore-oblique scope so that light is reflected and the image is viewed at approximately a 30° angle to the longitudinal axis. It should be noted that the endoscope is not part of the present invention and therefore neither its internal components or its function will be discussed in detail herein.

Sheath 14 preferably is constructed of a transparent material such as glass or a high impact clear plastic sold under the trademark LEXAN®, manufactured by General Electric Company. The provision of a transparent material in the construction of obturator 14 permits 360° viewing of the surgical procedure at the surgical site as will be discussed below. The sheath is preferably 6mm in diameter. The conical shaped distal tip portion 16 of sheath 14 is configured and dimensioned for blunt dissection and displacement of tissue as the instrument 10 is inserted.

As will be seen with reference to FIGS. 4 and 6, a longitudinal bore 53 is provided through the length of sheath 14 which communicates with a longitudinal bore 52 in handle 12, where the bore opens to the exterior at opening 26 in locking nut 18. The bore has an internal diameter slightly larger than the outer diameter of the endoscope 24. The endoscope 24 is inserted through opening 26 and through the bores 52, 53 of the handle 12 and sheath 14. As will be described below, locking nut 18 secures endoscope 24 to instrument 10.

With continued reference to FIGS. 4 and 6, also within sheath 14 is blade 40, which is secured at connection point 44 to actuation knob 22 through the provision of blade arm 42. The proximal end of blade arm 42 is preferably pinned to knob 22 via holding pin 44, but can be attached by other means such as by welding. Blade arm 42 extends longitudinally along a boom wall of sheath 14 to provide clear passage of endoscope 24 through longitudinal bore 53. Reciprocal movement of blade arm 42 causes corresponding movement of blade 40.

FIGS. 4 and 5 illustrate the cutting blade 40 in its protected position fully enclosed within sheath 14. In this position, the blade 40 sits within nodule or shroud 43 and is shielded by the top wall and side walls of the shroud and is distal of opening 20 in sheath 14 so that the cutting edge 41 is not exposed. The cutting edge 41 of blade 40 slopes slightly toward the distal direction to facilitate cutting. Surface 46 is of reduced diameter (curves downwardly) to improve visibility and to permit tissue to be directed into the opening 20 to be engaged by blade 40.

Figure 7:
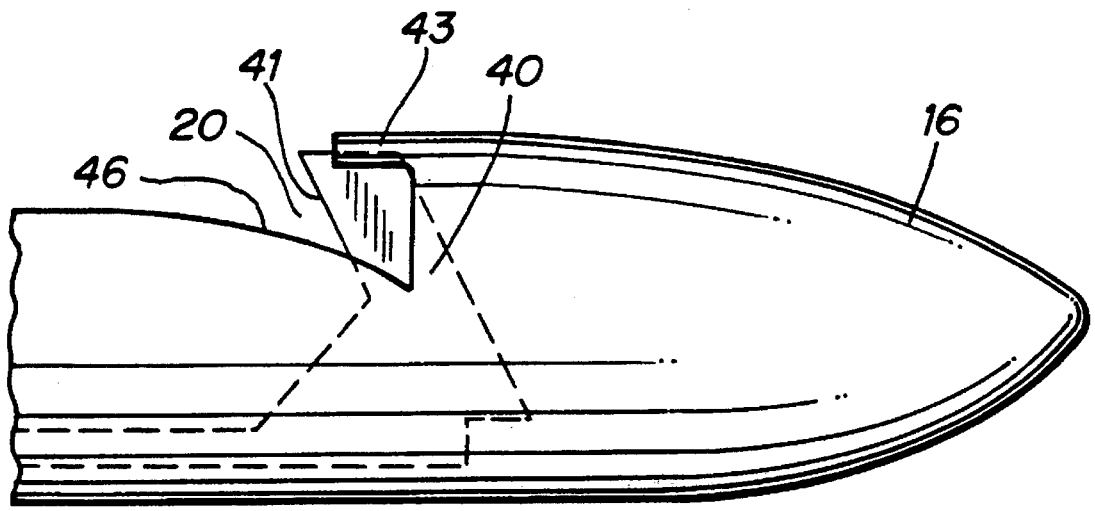
FIG. 7 is an enlarged view of the distal end of the instrument of the present invention showing the blade (in phantom) in the position of FIG. 6.

FIGS. 6 and 7 illustrate blade 40 in the armed (deployed) position where it is moved proximally through the opening 20 to expose the cutting edge 41. In this position the cutting edge 41 has been moved through opening 20 to an exposed position, proximal of opening 20, in order to engage tissue; however the blade 40 remains shielded by the top and side walls of shroud 43. As noted above, this movement of the cutting edge between retracted and deployed positions is achieved by sliding movement of actuation knob 22. Clearly, other mechanisms can be used to achieve the function of moving the cutting blade between the fully protected and deployed positions.

A spring loaded detent mechanism is provided to indicate to the user that the blade arm is in the protected and deployed positions. More specifically, transverse pin 60, biased by spring 64, extends into slot 61 in knob 22. Holding pin 44 is positioned through slot 61 such that when the blade 40 is in the protected position, holding pin 44 biases transverse pin 60 upwardly (see arrow S, FIG. 4). When knob 22 is moved proximally to deploy the blade 40, holding pin 44 slides proximally allowing transverse pin 60 to slide downwardly into slot 61. This provides a tactile feel to the user to indicate that blade 40 has been deployed.

Turning now to the securement of the endoscope 24 within longitudinal bores 52, 53, locking nut 18 is positioned at the distal end of the handle 10 and has threads 50 cooperating with internal threads 51 of handle 10 (see FIGS. 4 and 6). After endoscope 24 is positioned in the longitudinal bores, nut 18 is rotated to compress O-ring 54 which due to its compression will engage endoscope 24 to secure endoscope 24 to the handle 12. Rotating nut 18 in the opposite direction decompresses O-ring 54 and allows for removal of the endoscope. To obtain maximum visibility, the knife of the present invention is preferably positioned in sheath 14 such that the bottom angle of incidence of the light emitted by 30° endoscope 24, indicated by arrow A in FIG. 6, hits the bottom of the knife blade 40.

An alternative mode of securing the endoscope 24 to the instrument is illustrated in FIG. 8. A collet 70 is positioned within internal portion 72 of handle 10. The endoscope 24 is inserted through handle 10 (and collet 70) and sheath 14. The threads of locking nut 18 engage the internal threads of handle 10. Rotation of locking nut 18 slides collet 70 distally to thereby constrict its diameter as its fingers are forced inwardly by the tapered surface 72 of handle 10. Thus, collet 70 clamps down on the endoscope 24 to secure it to instrument 10. Clearly, other ways of securing the scope, such as a latch mechanism, a friction fit, etc. can be utilized.

With respect to FIG. 3, the cutting instrument 10 of the present invention is particularly suited for surgical procedures to release the pressure in the carpal tunnel, to provide relief from carpal tunnel syndrome. The carpal tunnel in the hand is defined by the space between the carpal bones and the transverse carpal ligament, and it is through this tunnel that the median nerve passes. Through repetitive motion, the median nerve may become irritated, and the transverse carpal ligament may thicken to compress the space in the carpal tunnel and further irritate the median nerve. Irritation of this nerve may lead to paresthesia in the hand, characterized by nocturnal pain, numbness and weakening of the grip of the fingers. As seen in FIG. 3, hand 30 is shown with the palm facing upward and a section of the palm removed to show transverse carpal ligament 32. It is beneath this ligament that the carpal tunnel allows the median nerve to pass.

With reference to FIGS. 3—5, in use, instrument 10 is slid over conventional endoscope 24 and locking nut 18 is rotated to clamp onto the scope for secure attachment An incision is made at the base of wrist 34 so that sheath 14 may be inserted into the incision. Tapered tip 16 dissects and displaces tissue as the instrument 10 is advanced towards through the carpal tunnel beneath transverse carpal ligament 32. The configuration of tip 16 also prevents snagging or damaging the tissue. Once tip 16 passes completely through the carpal tunnel, the edge 33 of the transverse carpal ligament on the finger side of the ligament is positioned within opening 20 and guided into the opening by curved surface 46. At this time, actuation knob 22 is slid in a proximal direction (arrow B) to move blade 40 from the undeployed position shown in FIG. 5 to the exposed (deployed) position shown in FIG. 7. The entire procedure is viewed through the provision of endoscope 24 which is positioned in longitudinal bores 52, 53 so that the procedure may be viewed through the transparent sheath 14. After the blade is moved to the position shown in FIG. 5, the entire instrument (and endoscope) is withdrawn; i.e. moved proximally, so that cutting edge 41 of blade 40 engages and divides only the transverse carpal ligament 32 and does not engage any other tissue. Shroud 43 provides a surface for tissue to pass over the instrument without engaging blade 40. After the ligament is severed, the blade is returned to the position shown in FIG. 4 by distal movement of actuation knob 22 to its original position so that the instrument may be removed through the original incision in wrist 34.

While the invention has been particularly shown and described with reference to the preferred embodiments, it will be understood by those skilled in the an that various modifications and changes in form and detail may be made therein without departing from the scope and spirit of the invention. Accordingly, modifications such as elimination of the actuation knob so that the blade is positioned in an armed location at all times, as well as other modifications such as various means for securing the endoscope to the instrument, but not limited to these modifications, are to be considered within the scope of the invention.

What is claimed is:

1. A surgical cutting instrument comprising:

a sheath member defining a longitudinal axis having a proximal end and a closed distal end and an outwardly radially directed nodule tapered towards said distal end and defining a proximally directed opening, said opening being disposed in a plane which is at an angle with respect to the longitudinal axis; and a cutting member disposed within said sheath member having a proximally directed cutting edge disposed at an angle to the longitudinal axis, said cutting member being manipulable from a position spaced from said distal end and being movable from a first position wherein said cutting edge is fully enclosed within said sheath member to a second position wherein only said cutting edge is exposed at said opening of said nodule, said cutting edge retaining the same angle with respect to the longitudinal axis in each of said first and second positions and wherein the sheath member has a bore extending through the length thereof and to the cutting member, the bore having a diameter sufficient to receive a viewing member to enable viewing of the cutting edge.

2. An instrument according to claim 1, further comprising a viewing member disposed within said sheath member for viewing said cutting edge during a surgical procedure.

3. An instrument according to claim 1, further comprising a handle member secured to said proximal end of said sheath member, said handle member and said sheath member defining a longitudinal bore extending through said handle member to said closed distal end of said sheath member, said handle member including means for manipulating said cutting member.

4. An instrument according to claim 3, further comprising viewing means disposed within said longitudinal bore for viewing a surgical procedure.

5. An instrument according to claim 4, wherein said sheath member is constructed of a transparent material.

6. An instrument according to claim 4, further comprising means for securing said viewing means to said handle member.

7. An instrument according to claim 2, wherein said sheath member is constructed of a transparent material.

8. An instrument according to claim 1, wherein said distal end of said sheath member is substantially conically shaped.

9. An instrument according to claim 1, further comprising means for receiving viewing means.

10. An instrument according to claim 1, further comprising a detent mechanism for retaining said cutting member in said second position.

11. A surgical cutting instrument comprising:

a sheath member defining a longitudinal axis having a closed distal end and an outwardly radially directed nodule closed at a distal end and defining a proximally directed opening, said opening defining a plane which is at an angle with respect to the longitudinal axis; and a cutting member disposed within said sheath member and having a proximally directed cutting edge disposed at an angle to the longitudinal axis, said cutting edge being disposed adjacent to and within said opening of said nodule, the angle of said cutting edge with respect to the longitudinal axis being substantially equal to the angle of the plane of said opening with respect to the longitudinal axis.

12. An instrument according to claim 11, further comprising means for moving said cutting edge.

13. An instrument according to claim 11, further comprising a handle disposed at a proximal end of said sheath member and said sheath member and said handle define a longitudinal bore extending through said handle and into said sheath member.

14. An instrument according to claim 13, further comprising viewing means disposed in said bore for viewing a surgical procedure, said handle including means for securing said viewing means in said bore.

15. An instrument according to claim 14, wherein said sheath member is constructed of a transparent material.

16. An instrument according to claim 11, further comprising means disposed in said sheath member for receiving viewing means for viewing a surgical procedure.

17. A surgical cutting instrument comprising:

a handle having a longitudinal bore;

an endoscopic portion extending from said handle having a longitudinal bore in communication with said bore in said handle, said endoscopic portion having a closed distal end remote from said handle and a proximally directed opening defining a plane which is at an angle with respect to the longitudinal bore of siad endosepic portion; and a cutting member including a cutting edge disposed at an angle to the longitudinal bore of siad endoscopic portion and being disposed within said endoscopic portion and movable from a first position wherein said cutting member is fully enclosed within said endoscopic portion to a second position wherein only said cutting edge is exposed at said opening on said endoscopic portion, and wherein said cutting edge retains the same angle with respect to the longitudinal bore of siad endoscopic portion in each of said first and second positions, the longitudinal bore in said endoscopic portion extending to the cutting member and having a diameter sufficient to receive viewing means to enable viewing of the cutting edge.

18. An instrument according to claim 17, further comprising viewing means disposed in said longitudinal bore of siad endoscopic portion for viewing a surgical procedure.

19. An instrument according to claim 18, wherein said endoscopic portion is constructed of a transparent material.

20. An instrument according to claim 18, further comprising means for securing said viewing means in said longitudinal bore of said handle.

21. An instrument according to claim 17, wherein said distal end of said endoscopic portion is substantially conically shaped.

22. An instrument according to claim 17, wherein said handle includes means for manipulating said cutting member.

23. A surgical cutting instrument comprising:

an endoscopic portion having a longitudinal bore and an opening facing in a proximal direction in a plane which is at an angle to the longitudinal bore;

means for securing an endoscope within said bore; and a cutting member including a cutting edge disposed at an angle to the bore at said opening within said endoscopic portion and positioned proximally of a distal tip of said endoscopic portion, said cutting member being movable from a first position wherein said cutting edge is fully enclosed within said endoscopic portion to a second position wherein only said cutting edge is exposed at the opening of said endoscopic portion, and wherein said cutting edge is exposed in said proximal direction when said cutting member is in said second position.

24. An instrument according to claim 23, wherein said securing means comprises a O-ring and means for compressing said O-ring.

25. An instrument according to claim 23, further comprising a handle member having a longitudinal bore communicating with said bore of said endoscopic portion, and means positioned on said handle for moving said cutting member.

26. An instrument according to claim 23, wherein said endoscopic portion is constructed of a transparent material.

27. An instrument according to claim 23, wherein said securing means comprises a collet and means for compressing said collet.

28. An instrument according to claim 27, wherein said compressing means comprises an internal tapered surface on said handle member.

29. A surgical cutting instrument comprising:

a sheath member having a closed distal end and defining a longitudinal axis;

a cutting member positioned within said sheath member, said cutting member movable between an undeployed and a deployed position and having a proximally facing cutting edge disposed at an angle to the longitudinal axis, said cutting edge being disposed at said angle to the longitudinal axis in each of said undeployed and deployed positions;

means for receiving a viewing instrument to allow visualization of said cutting member; and means for securing the viewing instrument to the surgical cutting instrument.

30. An instrument according to claim 29, further comprising a handle member, said sheath member extending from said handle member.

31. An instrument according to claim 30, further comprising means positioned on said handle member for moving said cutting member.

32. An instrument according to claim 31, wherein said receiving means comprises a longitudinal bore formed in said sheath member.

33. A method for decompression of the carpal tunnel through division of the transverse carpal ligament comprising the steps of:

incising the wrist of a patient adjacent the carpal tunnel;

inserting a cutting instrument into the carpal tunnel beneath the transverse carpal ligament to a position beyond the transverse carpal ligament, said instrument having a sheath including a proximally directed opening defining a plane which is at an angle to a longitudinal axis of the sheath and a proximally directed cutting blade disposed at an angle to the longitudinal axis and positioned adjacent said opening, the angle of said cutting blade with respect to the longitudinal axis being substantially equal to the angle of the plane of said opening with respect to the longitudinal axis;

moving a cutting edge of said cutting blade adjacent said opening;

engaging said transverse carpal ligament with said cutting edge; and withdrawing said instrument, such that said cutting edge divides said ligament to decompress the carpal tunnel.

34. The method of claim 33, further comprising viewing said inserting and engaging steps through an endoscope, said endoscope being positioned within said sheath of said instrument.

\* \* \* \* \*